United States Patent
Yang et al.

(10) Patent No.: US 12,170,149 B2
(45) Date of Patent: Dec. 17, 2024

(54) METHOD AND APPARATUS FOR CONSTRUCTING DRUG KNOWLEDGE GRAPH

(71) Applicant: Beijing Jingdong Tuoxian Technology Co., Ltd., Beijing (CN)

(72) Inventors: Shuai Yang, Beijing (CN); Pei Xie, Beijing (CN); Hao Wen, Beijing (CN); Lei Han, Beijing (CN); Ya Zhang, Beijing (CN)

(73) Assignee: Beijing Jingdong Tuoxian Technology Co., Ltd., Beijing (CN)

( * ) Notice: Subject to any disclaimer, the term of this patent is extended or adjusted under 35 U.S.C. 154(b) by 194 days.

(21) Appl. No.: 18/016,896

(22) PCT Filed: Apr. 22, 2021

(86) PCT No.: PCT/CN2021/088889
§ 371 (c)(1),
(2) Date: Jan. 19, 2023

(87) PCT Pub. No.: WO2022/021958
PCT Pub. Date: Feb. 3, 2022

(65) Prior Publication Data
US 2023/0352192 A1  Nov. 2, 2023

(30) Foreign Application Priority Data
Jul. 30, 2020 (CN) .......................... 202010750770.3

(51) Int. Cl.
*G16H 70/40* (2018.01)

(52) U.S. Cl.
CPC .................................. *G16H 70/40* (2018.01)

(58) Field of Classification Search
CPC ...... G16H 70/40; G06F 16/367; G06F 40/295
See application file for complete search history.

(56) References Cited

U.S. PATENT DOCUMENTS

| 10,706,104 B1 | 7/2020 | Lee et al. |
| 2016/0364377 A1 | 12/2016 | Krishnamurthy |

(Continued)

FOREIGN PATENT DOCUMENTS

| CN | 104933024 A | 9/2015 |
| CN | 108073569 A | 10/2016 |

(Continued)

OTHER PUBLICATIONS

International Search Report for PCT/CN2021/088889, dated Jul. 22, 2021, 4 pgs.

*Primary Examiner* — Chinyere Mpamugo
(74) *Attorney, Agent, or Firm* — BLANK ROME LLP

(57) ABSTRACT

A method and apparatus for constructing a drug knowledge graph are provided. The method may include: identifying entities in a drug text; replacing medical key entities among the entities with character strings that conform to a preset rule, to obtain a replaced text; restoring the character strings in a word segmentation result, determined based on the replaced text, to the medical key entities replaced by the character strings; forming a linear entity relationship between the entities based on the entities; and generating a drug knowledge graph according to a parsing result obtained by syntactically parsing the linear entity relationship.

19 Claims, 8 Drawing Sheets

(56) References Cited

U.S. PATENT DOCUMENTS

2017/0300469 A1    10/2017  Mirhaji
2019/0171656 A1*    6/2019  Zhang .................... G16H 20/90
2021/0210213 A1*    7/2021  Dai ....................... G16H 10/60

FOREIGN PATENT DOCUMENTS

| CN | 109192321 A | 1/2019 |
| CN | 109284396 A | 1/2019 |
| CN | 109509556 A | 3/2019 |
| CN | 110377755 A | 10/2019 |
| CN | 110390021 A | 10/2019 |
| CN | 112307216 A | 2/2021 |

* cited by examiner

METHOD AND APPARATUS FOR CONSTRUCTING DRUG KNOWLEDGE GRAPH

CROSS-REFERENCE TO RELATED APPLICATIONS

This patent application is a National Stage of International Application No. PCT/CN2021/088889, filed Apr. 22, 2021, which claims priority to Chinese Patent Application No. 202010750770.3 filed on Jul. 30, 2020 by the applicant Beijing Jingdong Tuoxian Technology Co., Ltd., and entitled "Method and Apparatus for Constructing Drug Knowledge Graph", the contents of which are incorporated herein by reference in their entireties.

TECHNICAL FIELD

The present disclosure relates to the field of computer technology, specifically to the field of knowledge graph technology, and in particular, to a method and apparatus for constructing a drug knowledge graph, an electronic device, and a computer-readable medium.

BACKGROUND

The knowledge graph is a branch of knowledge engineering in artificial intelligence, and it has a relatively mature application in the general field. The usage and dosage section of a drug instruction has its unique abbreviated form and syntactic structure on the basis of general syntax rules.

SUMMARY

Embodiments of the present disclosure provides a method and apparatus for constructing a drug knowledge graph, an electronic device, and a computer-readable medium.

In a first aspect, an embodiment of the present disclosure provides a method for constructing a drug knowledge graph, the method including: identifying entities in a drug text; replacing medical key entities among the entities with character strings that conform to a preset rule, to obtain a replaced text; restoring the character strings in a word segmentation result, determined based on the replaced text, to the medical key entities replaced by the character strings; forming a linear entity relationship between the entities based on the entities; and generating a drug knowledge graph according to a parsing result obtained by syntactically parsing the linear entity relationship.

In some embodiments, the method further includes: establishing a mapping relationship table between the character strings and the medical key entities replaced by the character strings.

In some embodiments, the method further includes: identifying medical non-key entities in the word segmentation result. The forming a linear entity relationship between the entities based on the entities includes: sorting the medical key entities and the medical non-key entities according to orders of the entities in the drug text, to obtain the linear entity relationship corresponding to the drug text.

In some embodiments, the medical key entities comprise: disease name and drug name; and the medical non-key entities comprise: crowd, dosage, frequency, treatment course, administration route, and administration time.

In some embodiments, the entities comprise precondition entities, and usage and dosage entities, and the precondition entities comprise the medical key entities. The generating a drug knowledge graph according to a parsing result obtained by syntactically parsing the linear entity relationship includes: obtaining a precondition merging result based on the precondition entities obtained by identifying the linear entity relationship; obtaining a usage and dosage merging result based on the usage and dosage entities obtained by identifying the linear entity relationship; based on positional relationship between each precondition entity and each usage and dosage entity in the linear entity relationship, combining the precondition merging result and the usage and dosage merging result to obtain a root node set in which at least one element in the precondition merging result and at least one element in the usage and dosage merging result are used as set elements; merging all different set elements in the root node set; and taking a merging result with a highest merging probability among merging results of the root node set as the parsing result, and adding the parsing result to the drug knowledge graph.

In some embodiments, the obtaining a precondition merging result based on the precondition entities obtained by identifying the linear entity relationship includes: identifying the precondition entities in the linear entity relationship, and taking each precondition entity among the identified precondition entities and combinations between the precondition entities as set elements to form a precondition entity set; and merging all different set elements in the precondition entity set to obtain the precondition merging result.

In some embodiments, the obtaining a usage and dosage merging result based on the usage and dosage entities obtained by identifying the linear entity relationship includes: identifying the usage and dosage entities in the linear entity relationship, and taking each usage and dosage entity among the identified usage and dosage entities and combinations between the usage and dosage entities as set elements to form a usage and dosage entity set; and merging all different set elements in the usage and dosage entity set to obtain the usage and dosage merging result.

In some embodiments, the method further includes: identifying attributes of the entities in the drug text; and adding the attributes of the entities to the drug knowledge graph.

In some embodiments, the method further includes: performing at least one of following formatting processes on the drug text: normalizing different punctuation marks representing a same meaning in the drug text; or converting Chinese numbers in the drug text into Arabic numbers.

In a second aspect, an embodiment of the present disclosure provides an apparatus for constructing a drug knowledge graph, the apparatus including: an identification unit, configured to identify entities in a drug text; a replacement unit, configured to replace medical key entities among the entities with character strings that conform to a preset rule, to obtain a replaced text; a restoration unit, configured to restore the character strings in a word segmentation result, determined based on the replaced text, to the medical key entities replaced by the character strings; a forming unit, configured to, based on the entities, form a linear entity relationship between the entities; and a parsing unit, configured to generate a drug knowledge graph according to a parsing result obtained by syntactically parsing the linear entity relationship.

In some embodiments, the apparatus further includes: a mapping unit, configured to establish a mapping relationship table between the character strings and the medical key entities replaced by the character strings.

In some embodiments, the apparatus further includes: a distinguishing unit, configured to identify medical non-key entities in the word segmentation results; and the forming unit is further configured to sort the medical key entities and the medical non-key entities according to the order of the entities in the drug text, to obtain the linear entity relationship corresponding to the drug text.

In some embodiments, the medical key entities include: disease name and drug name; and the medical non-key entities include: crowd, dosage, frequency, treatment course, administration route, and administration time.

In some embodiments, the entities include precondition entities and usage and dosage entities; the precondition entities include the medical key entities; and the parsing unit includes: a precondition extraction module configured to obtain a precondition merging result based on the precondition entities obtained by identifying the linear entity relationship, a usage and dosage obtaining module configured to obtain a usage and dosage merging result based on the usage and dosage entities obtained by identifying the linear entity relationship, a combination module configured to, based on the positional relationship between each precondition entity and each usage and dosage entity in the linear entity relationship, combine the precondition merging result and the usage and dosage merging result to obtain a root node set in which at least one element in the precondition merging result and at least one element in the usage and dosage merging result are used as set elements; a merging module configured to merge all different set elements in the root node set, a parsing module configured to take a merging result with the highest merging probability among merging results of the root node set as the parsing result, and a adding module configured to add the parsing result to the knowledge graph.

In some embodiments, the precondition extraction module includes: a pre-identification submodule configured to identify the precondition entities in the linear entity relationship, a pre-combination submodule configured to take each precondition entity among the identified precondition entities and combinations between the precondition entities as set elements to form a precondition entity set, and a pre-merging submodule configured to merge all different set elements in the precondition entity set to obtain the precondition merging result.

In some embodiments, the usage and dosage obtaining module includes: a usage and dosage identification submodule configured to identify the usage and dosage entities in the linear entity relationship, a dosage combination submodule configured to take each usage and dosage entity among the identified usage and dosage entities and combinations between the usage and dosage entities as set elements to form a usage and dosage entity set, and a usage and dosage merging submodule configured to merge all different set elements in the usage and dosage entity set to obtain the usage and dosage merging result.

In some embodiments, the apparatus further includes: a distinguishing unit configured to identify attributes of the entities in the drug text, and a adding unit configured to add the attributes of the entities to the drug knowledge graph.

In some embodiments, the apparatus further includes: a formatting unit configured to normalize different punctuation marks representing the same meaning in the drug text, and a conversion unit configured to convert Chinese numbers in the drug text into Arabic numbers.

In a third aspect, an embodiment of the present disclosure provides an electronic device. The electronic device includes: one or more processors; and a storage apparatus on which one or more programs are stored. The ne or more programs, when executed by the one or more processors, cause the one or more processors to implement the method in any implementation according to the first aspect.

In a fourth aspect, an embodiment of the present disclosure provides a computer-readable medium storing a computer program. When the program is executed by a processor, the method in any implementation according to the first aspect is implemented.

BRIEF DESCRIPTION OF THE DRAWINGS

After reading detailed descriptions of non-limiting embodiments with reference to the following accompanying drawings, other features, objectives and advantages of the present disclosure will become more apparent.

DETAILED DESCRIPTION OF EMBODIMENTS

The present disclosure will be further described below in detail in combination with the accompanying drawings and the embodiments. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that the embodiments in the present disclosure and the features in the embodiments may be combined with each other on a non-conflict basis. The present disclosure will be described below in detail with reference to the accompanying drawings and in combination with the embodiments.

Figure 1:
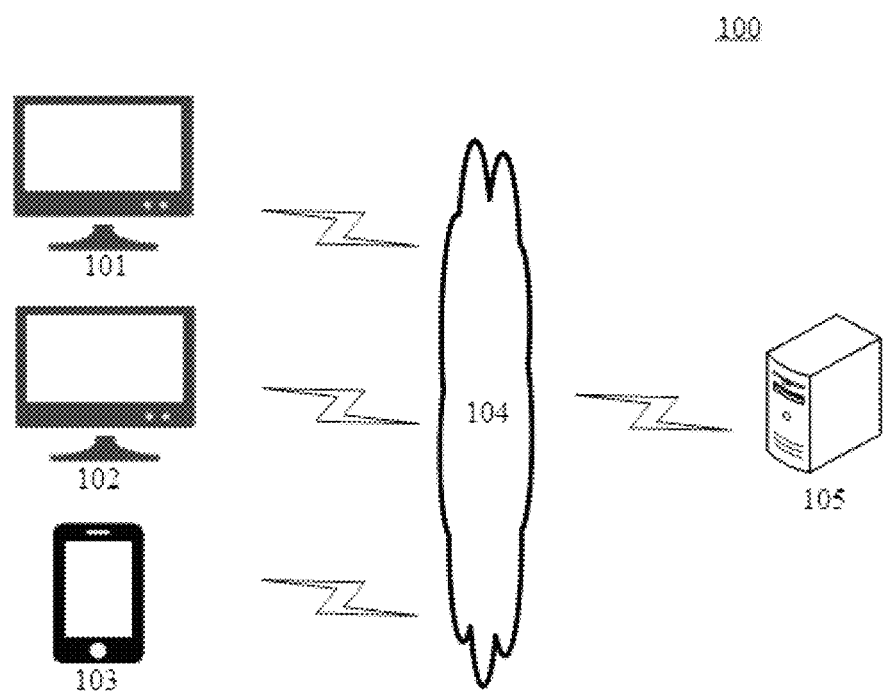
FIG. 1 is an architectural diagram of an exemplary system to which an embodiment of the present disclosure may be applied.

FIG. 1 illustrates an exemplary system architecture 100 to which a method for constructing a drug knowledge graph according to the present disclosure may be applied.

As shown in FIG. 1, the system architecture 100 may include a terminal device 101, 102 or 103, a network 104, and a server 105. The network 104 serves as a medium providing a communication link between the terminal device 101, 102 or 103 and the server 105. The network 104 may include various connection types, and may usually include wireless communication links and the like.

The terminal device 101, 102 or 103 may interact with the server 105 through the network 104 to receive or send messages, etc. The terminal device 101, 102 or 103 may be installed with various communication client applications, such as instant messaging tools and e-mail clients.

The terminal device 101, 102 or 103 may be hardware or software. When the terminal device 101, 102 or 103 is hardware, the terminal device may be user equipment with communication and control functions, and the user equipment may communicate with the server 105. When the terminal device 101, 102 or 103 is software, the terminal device may be installed in the user equipment. The terminal device 101, 102 or 103 may be implemented as a plurality of software programs or software modules (for example, a plurality of software programs or software modules for providing distributed services), or as a single software program or software module, which is not limited herein.

The server 105 may be a server that provides various services, for example, a knowledge graph server that provides support for a knowledge graph system on the terminal device 101, 102 or 103. The knowledge graph server may analyze and process relevant information of each target image in the network, and feed back the processing result (such as the generated knowledge graph) to the terminal device.

It should be noted that the server may be hardware or software. When the server is hardware, the server may be implemented as a distributed server cluster composed of multiple servers, or implemented as a single server. When the server is software, the server may be implemented as a plurality of software programs or software modules (e.g., software programs or software modules for providing distributed services), or as a single software program or software module. Specific limitations are not provided here.

It should be noted that, the method for constructing a drug knowledge graph, provided by the embodiments of the present disclosure, is generally performed by the server 105.

It should be understood that the numbers of the terminal devices, the network and the server in FIG. 1 are merely illustrative. Any number of terminal devices, networks and servers may be provided based on actual requirements.

In entity hospitals and Internet hospitals, doctors may issue a large number of drug prescriptions every day. Whether the usage and dosage of drugs in these prescriptions are reasonable requires the review of pharmacists. However, the review of the large number of drug prescriptions brings great workload and burden to the pharmacists. However, a drug knowledge graph may be generated from the drug prescriptions, and when the knowledge graph is applied, the corresponding usage and dosage of a patient can be matched according to the patient's personal situation, and items to be selected are given for the pharmacist to screen, which can help the pharmacist reduce the workload and save the review time.

Figure 2:
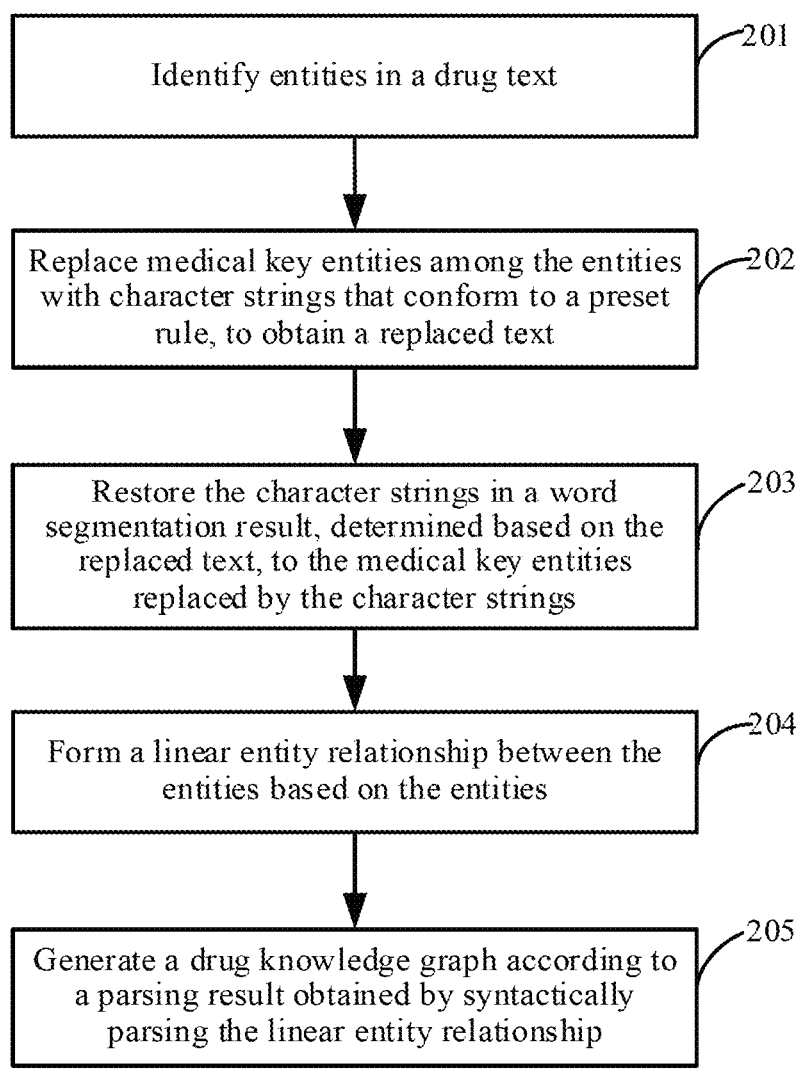
FIG. 2 is a flowchart of an embodiment of a method for constructing a drug knowledge graph according to the present disclosure.

FIG. 2 shows a flow 200 of an embodiment of a method for constructing a drug knowledge graph according to the present disclosure. The method for constructing a drug knowledge graph includes the following steps.

Step 201: Identify entities in a drug text.

In this embodiment, an executing body (for example, the server or the terminal device) on which the method for constructing a drug knowledge graph runs may acquire the drug text by means of real-time acquisition or memory reading.

The drug text includes drugs used to treat different diseases of different crowds and the usage and dosage of various drugs. The drug text may be a drug instruction on a medicine box, or a drug prescription. For example, a drug instruction is: "oral, two tablets once a day for adults; one tablet once a day for children".

Because the drug text includes drugs used to treat different diseases of different crowds and the usage and dosage of various drugs, the entities in the drug text may include: crowd, disease name, drug name, dosage, frequency, treatment course, administration route, administration time, conjunctions, and the like.

For the exclusivity of drugs or diseases, in order to facilitate identification on the entities, in some optional implementations of this embodiment, the entities may be classified into medical key entities and medical non-key entities. The medical key entities are medical proper nouns, for example, the medical key entities include: drug name and disease name. The medical non-key entities are not medical proper nouns, but are common nouns in the drug text, such as dosage, treatment course, administration route, and the like.

In some optional implementations of this embodiment, the medical key entities include: drug name and disease name; and the medical non-key entities include: crowd, dosage, frequency, treatment course, administration route, and administration time. The medical key entities and medical non-key entities provided in this optional implementation may cover the types of entities in a drug instruction, which ensures the comprehensiveness of entity type division.

In this embodiment, identifying entities in a drug text may be identifying medical key entities, or identifying medical key entities and medical non-key entities. The identification on the medical key entities may be implemented by lexicographic enumeration. The enumeration is used to examine the situation that each entity belongs to a medical key entity one by one, and the lexicographic enumeration identification on a disease name in the medical key entities is performed through a maintained dictionary table of diseases. For the drug text, the dictionary table of diseases is traversed. If a word A in the dictionary table is in the drug text, the word A in the drug text is marked as a disease name.

In order to facilitate syntactic parsing on the entities, Alternatively, the entities may also be classified into precondition entities and usage and dosage entities. The precondition entities are used to represent a drug, a disease, drug usage or subjects suffering from a certain disease, for example, crowds, a disease name, a drug name, and conjunctions between the aforementioned three. The precondition entities include the medical key entities. The usage and dosage entities are entities related to drug usage, such as frequency, treatment course, administration route, administration time, and conjunctions between the aforementioned four.

Different drug texts include different entities. Some drug texts may include precondition entities and usage and dosage entities, and some drug texts may include usage and dosage entities.

In this embodiment, identifying entities in a drug text may be identifying precondition entities, or identifying usage and dosage entities.

Step 202: Replace medical key entities among the entities with character strings that conform to a preset rule, to obtain a replaced text.

In this optional implementation, because the drug is a proper noun, has certain complexity and may affect subsequent generation of a drug knowledge graph, the identified medical key entities need to be replaced.

During the replacement of the medical key entities, characters corresponding to the medical key entities that conform to the preset rule are generated after the medical key entities are identified, and a corresponding relationship between the character strings that conform to the preset rule and the medical key entities is recorded in real time.

In this embodiment, the generated character strings that conform to the preset rule may be self-defined character strings with certain rule, and different character strings may be defined for distinguishing different types of medical key entities. For example, a drug text is: "treat pertussis: once a day, one tablet at a time". It is identified that "pertussis" is a medical key entity, and a character string "indication_0" is defined to replace "pertussis" to obtain a replaced text "indication_0: once a day, one tablet at a time".

Alternatively, the character strings that conform to the preset rule may also be automatically assigned by a character template and conform to the preset rule, and the character template may also record a corresponding relationship between the character strings that conform to the preset rule and the medical key entities. After the character strings of the preset rule replace the medical key entities among the entities, the corresponding relationship between the character strings of the preset rule and the medical key entities may be obtained through the template, so as to restore the medical key entities.

Step 203: Restore character strings in a word segmentation result, determined based on the replaced text, to the medical key entities replaced by the character strings.

In this embodiment, word segmentation is first performed on the replaced text to identify the character strings that conform to the preset rule in the word segmentation result of the replaced text, and the character strings that conform to the preset rule are restored to the medical key entities.

Specifically, word segmentation may be performed on the replaced text by means of a Chinese word segmentation function of a Chinese word segmentation tool to obtain a word segmentation result. The Chinese word segmentation is to segment a Chinese character sequence to obtain individual words. Further, available Chinese word segmentation tools include: jieba, SnowNLP (Simplified Chinese Text Processing), etc.

Step 204: Based on the entities, form a linear entity relationship between the entities.

In this embodiment, the entities identified in the drug text may be sorted according to the positions of the entities in the drug text to form the linear entity relationship between the entities. For example, a drug text is: "oral, once a day for adults, two tablets at a time; once a day for children, one tablet at a time". After entity identification, a linear entity relationship between the entities is formed as: {administration route: oral} {crowd: adults} {frequency: once a day} {dosage: two tablets at a time} {crowd: children} {frequency: once a day} {dosage: one tablet at a time}.

Alternatively, the entities identified in the drug text may also be formatted (for example, removal of text spaces, full-width half-width conversion, conversion of Chinese numbers into Arabic numbers, and normalization of symbols), and the formatted results are sorted according to the positions of the entities in the drug text to form a linear entity relationship between the entities. For example, a drug text is: "oral, once a day for adults, two tablets at a time; once a day for children, one tablet at a time". After the formatting of Chinese numbers into Arabic numbers, a linear entity relationship between the entities is formed as: {administration route: oral} {crowd: adults} {frequency: 1 time 1 day} {dosage: 2 tablets 1 time} {crowd: children} {frequency: 1 time 1 day} {dosage: 1 tablet 1 time}.

Step 205: Generate a drug knowledge graph according to a parsing result obtained by syntactically parsing the linear entity relationship.

In this embodiment, syntactically parsing the linear entity relationship refers to extracting, according to the type of each entity and a syntax rule between the entities and in combination with a preset syntactic parsing algorithm, an entity relationship that can best express the drug text from the linear entity relationship. The syntax parsing process is to parse the linear entity relationship into a tree-like entity relationship, and is also a process of converting the natural language of the drug text into a data structure that can be identified by a computer.

The preset syntactic parsing algorithm may include rule-based syntactic parsing and/or statistics-based syntactic parsing. For a given input text, the rule-based syntactic parsing is to map the input text to parsing results based on a written knowledge base rule; and the statistics-based syntactic parsing is to exhaust all possible parsing results and find the one with the maximum probability.

In this embodiment, because the entities in the drug text are for a drug, and the drug has a unique abbreviated form and syntax (for example, usage and dosage, etc.), the preset syntactic parsing algorithm may further use rule-based syntactic parsing and statistics-based syntactic parsing, thus making full use of the rigor of rule writing and the flexibility of statistical analysis.

For example, a drug text is: "oral, once a day for adults, two tablets at a time; once a day for children, one tablet at a time".

After the formatting of Chinese numbers into Arabic numbers, a linear entity relationship between the entities is formed as: {administration route: oral} {crowd: adults} {frequency: 1 time 1 day} {dosage: 2 tablets 1 time} {crowd: children} {frequency: 1 time 1 day} {dosage: 1 tablet 1 time}.

A tree-like relationship obtained after syntactic parsing is as follows.

{Administration route: oral}
  {Crowd: adults} {frequency: 1 time 1 day} {dosage: 2 tablets at a time}
  {Crowd: children} {frequency: 1 time 1 day} {dosage: 1 tablet 1 time}.

The drug knowledge graph generated by syntactically parsing the linear entity relationship retains the relationship between the entities in the linear entity relationship, which can ensure the accuracy and interpretability of drug knowledge graph mining results.

According to the method for constructing a drug knowledge graph provided by the embodiment of the present disclosure, entities in a drug text are first identified; second, medical key entities among the entities are replaced with character strings that conform to a preset rule, to obtain a replaced text; then, character strings in a word segmentation result determined based on the replaced text are restored to the medical key entities replaced by the character strings; next, based on the entities, a linear entity relationship between the entities is formed; and finally, a drug knowledge graph is generated according to a parsing result obtained by syntactically parsing the linear entity relationship. Therefore, before word segmentation is performed on the drug text, the medical key entities are first replaced with characters of the preset rule, which ensures the accuracy of word segmentation on the medical text; and the drug knowledge graph obtained by syntactic parsing on the basis of the linear entity relationship facilitates the conversation of a natural language of drug usage and dosage into a data structure that can be identified by a computer, which is beneficial to knowledge graph mining in the medical field and ensures the accuracy and interpretability of the drug knowledge graph.

Figure 3:
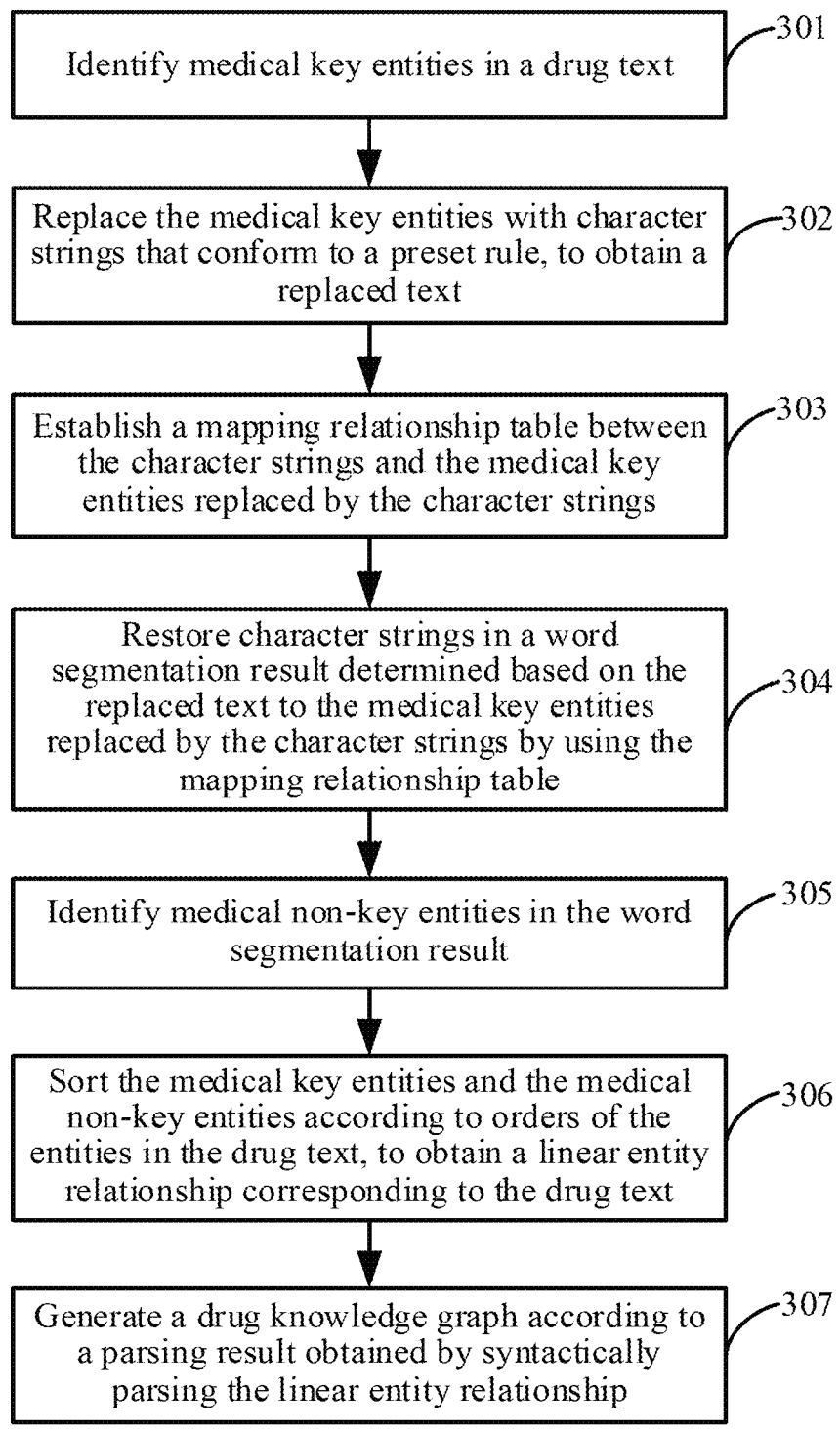
FIG. 3 is a flowchart of another embodiment of a method for constructing a drug knowledge graph according to the present disclosure.

In another embodiment of the present disclosure, the entities of the drug text include: medical keywords and medical non-key entities. With further reference to FIG. 3, a flow 300 of another embodiment of a method for constructing a drug knowledge graph according to the present disclosure is shown. The method for constructing a drug knowledge graph includes the following steps.

Step 301: Identify medical key entities in a drug text.

In this embodiment, the medical key entities may be identified by lexicographic enumeration. The enumeration is used to examine the situation that each entity belongs to a medical key entity one by one, and the lexicographic enumeration identification on a disease name in the medical key entities is performed through a maintained dictionary table of diseases. For the drug text, the dictionary table of diseases is traversed. If a word A in the dictionary table is in the drug text, the word A in the drug text is marked as a disease name.

Step 302: Replace the medical key entities with character strings that conform to a preset rule, to obtain a replaced text.

In this embodiment, because the medical proper nouns have certain complexity and may affect subsequent entity processing, the identified medical key entities need to be replaced.

The character string that conforms to the preset rule may be a self-defined character string, and different character strings may be defined for distinguishing different types of medical key entities. For example, a drug text is: "treat pertussis: once a day, one tablet at a time". It is identified that "pertussis" is a medical key entity, and a character string "indication_0" is defined to replace "pertussis" to obtain a replaced text "indication_0: once a day, one tablet at a time".

Step 303: Establish a mapping relationship table between the character strings and the medical key entities replaced with the character strings.

During the replacement of the medical key entities, characters corresponding to the medical key entities that conform to the preset rule may be generated after the medical key entities are identified, and a corresponding relationship between the character strings that conform to the preset rule and the medical key entities is recorded by the mapping relationship table in real time.

In this embodiment, establishing the mapping relationship between the character strings that conform to the preset rule and the medical key entities replaced by the character strings can facilitate subsequent restoration of the medical key entities.

For example, a drug text is: "treat pertussis: once a day, one tablet at a time". It is identified that "pertussis" is a medical key entity, and a character string "indication_0" is defined to replace "pertussis" to obtain a replaced text "indication_0: once a day, one tablet at a time". The established mapping relationship is: indication_0<->pertussis.

Step 304: Restore character strings in a word segmentation result determined based on the replaced text to the medical key entities replaced by the character strings by using the mapping relationship table.

In this embodiment, because the mapping relationship table records the mapping relationship between the character strings that conform to the preset rule and the medical key entities, after the character strings that conform to the preset rule are determined, the medical key entities corresponding to the character strings that conform to the preset rule can be obtained by looking up the mapping relationship table.

Step 305: Identify medical non-key entities in word segmentation results.

In this embodiment, a text template matching tool, such as a regular expression, may be used to write a template matching rule to identify other entities, namely medical non-key entities, except the medical key entities (drug name and disease name). Further, the medical non-key entities may also be identified by using an entity identification model. The entity identification model includes: a CRF (Conditional Random Fields) model, or a BERT (Bidirectional Encoder Representations from Transformers) model.

Because the expressions of these entities are limited in the usage and dosage section of the drug instruction, accurate identification can be achieved by template matching.

Step 306: Sort the medical key entities and the medical non-key entities according to the order of the entities in the drug text, to obtain a linear entity relationship corresponding to the drug text.

In this embodiment, the drug text is expressed as an abstract sentence composed of multiple entities in a linear relationship, that is, the linear entity relationship. The positional relationship between the entities in the linear entity relationship maintains the positional relationship between the entities in the drug text. The linear entity relationship can ensure that the information content of the drug text is not lost.

Step 307: Generate a drug knowledge graph according to a parsing result obtained by syntactically parsing the linear entity relationship.

The operation and feature of step 307 correspond to those of step 205 above, so the descriptions of the operation and feature in step 205 are also applicable to step 307.

According to the method for constructing a drug knowledge graph provided in this embodiment, a connection between the character strings and the medical key entities replaced with the character strings is established using the mapping relationship table before word segmentation of the drug text, which ensures the accuracy of word segmentation. Further, the identified medical key entities and medical non-key entities are sorted according to the order of each entity in the drug text, and the obtained linear entity relationship retains the positional relationship between the entities in the original drug text, which provides the basis for subsequent reorganization into a tree-like entity relationship.

Figure 4:
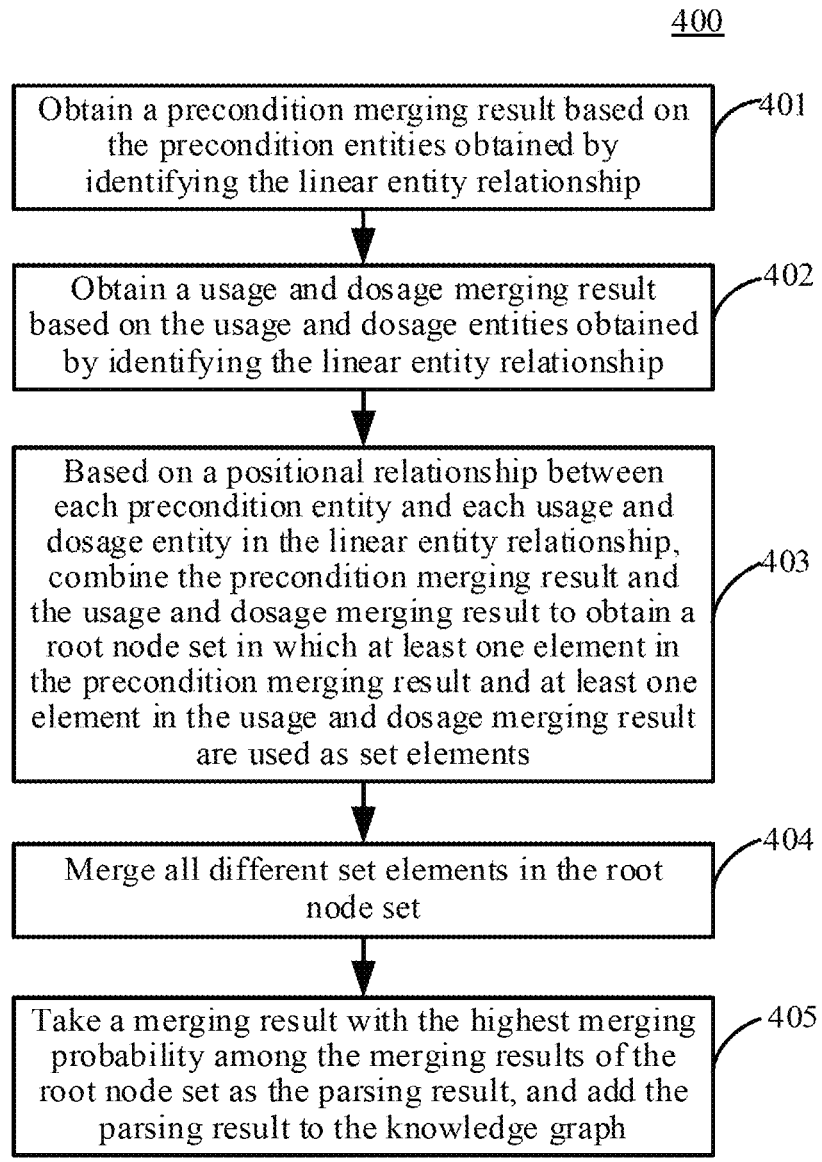
FIG. 4 is a flowchart of an embodiment of a method for generating a drug knowledge graph according to the present disclosure.

For the linear entity relationship including different types of entities, a drug knowledge graph with a tree-like entity relationship may be generated. In some optional implementations of this embodiment, the entities include precondition entities and usage and dosage entities, and the precondition entities include medical key entities. With further reference to FIG. 4, a flow 400 of an embodiment of a method for generating a drug knowledge graph is shown. The method for generating a drug knowledge graph includes the following steps.

Step 401: Obtain a precondition merging result based on the precondition entities obtained by identifying the linear entity relationship.

In this optional implementation, entities are classified into precondition entities and usage and dosage entities. The precondition entities are used to represent a drug, a disease, drug usage or subjects suffering from a certain disease, for example, crowds, a disease name, a drug name, and conjunctions between the aforementioned three.

In this optional implementation, after all the precondition entities in the linear entity relationship are identified, the identified different precondition entities may be merged (for example, two by two, or one by three, etc.) to obtain precondition merging sub-items, and multiple precondition merging sub-items are combined together to form a precondition merging result. The precondition merging result is a set with multiple precondition merging sub-items, and each precondition merging sub-item is an element in the precondition merging result.

Of course, according to the number of precondition entities identified, the precondition merging sub-items may also be a single precondition entity.

In some optional implementations of this embodiment, the obtaining a precondition merging result based on precondition entities obtained by identifying a linear entity relationship includes: identifying precondition entities in the linear entity relationship, and taking each precondition entity among the identified precondition entities and combinations between the precondition entities as set elements to form a precondition entity set; and merging all different set elements in the precondition entity set to obtain the precondition merging result.

In this optional implementation, all different set elements in the precondition entity set may be merged by combining a rule analysis method and a statistical analysis method. The rule analysis method is to comply with a preset rule, for example, the preset rule for merging the precondition entity set is: the precondition entity set can only include any one or more of three types of set elements: disease set elements, crowd set elements, and drug set elements. The disease set elements include a single disease name or multiple disease names connected by conjunctions. The crowd set elements include: a single crowd object or multiple crowd objects connected by conjunctions. The drug set elements include: a single drug name or multiple drug names connected by conjunctions.

The statistical analysis method may be an exhaustive method. The exhaustive method is to try all the possibilities. In the software, the outer loop is used to wrap the inner loop. When a certain jumping condition is satisfied, the inner loop and the outer loop are ended. All the different set elements that may be merged in the precondition entity set can be merged by the statistical analysis method.

According to the method for obtaining a precondition merging result provided by this alternative implementation, after precondition entities are identified, each precondition entity among the identified precondition entities and combinations between the precondition entities are taken as set elements to form a precondition entity set, and all different set elements in the precondition entity set are merged to obtain the precondition merging result, thereby providing a reliable sentence parsing mode for forming a tree-like entity relationship from the precondition entities and ensuring the reliability of a drug graph generated.

Step 402: Obtain a usage and dosage merging result based on the usage and dosage entities obtained by identifying the linear entity relationship.

In this embodiment, the usage and dosage entities are entities related to drug usage, such as frequency, treatment course, administration route, administration time, and conjunctions between the aforementioned four.

In this optional implementation, after all the usage and dosage entities in the linear entity relationship are identified, the identified different usage and dosage entities may be merged (for example, two by two, or one by three, etc.) to obtain usage and dosage merging sub-items, and multiple usage and dosage merging sub-items are combined together to form a usage and dosage merging result. The usage and dosage merging result is a set with multiple usage and dosage merging sub-items, and each usage and dosage merging sub-item is an element in the usage and dosage merging result.

Of course, according to the number of different usage and dosage entities identified, the usage and dosage merging sub-items may also be a single usage and dosage entity.

Step 403: Based on the positional relationship between each precondition entity and each usage and dosage entity in the linear entity relationship, combine the precondition merging result and the usage and dosage merging result to obtain a root node set in which at least one element in the precondition merging result and at least one element in the usage and dosage merging result are used as set elements.

In this alternative implementation, the set elements of the root node set are composed of at least one precondition merging sub-item in the precondition merging result and at least one usage and dosage merging sub-item.

Alternatively, each set element of the root node set may be expressed as a combination of 0 to 1 precondition merging sub-item and one or more usage and dosage merging sub-items.

For example, a linear entity relationship includes: "adult (PP1) once a day (MM1), two tablets at a time (MM2); children (PP2) once a day (MM3), one tablet at a time (MM4)", where the precondition merging result is: {[PP1] [PP2]}.

The usage and dosage merging result is: {[MM1 MM2] [MM3 MM4]; [MM1, MM2] [MM3 MM4]; [MM1][MM2 MM3][MM4]; [MM1][MM2 MM3] [MM4]; [MM1 MM2] [MM3 MM4]; [MM1 MM2] [MM3 MM4]}.

Based on the positional relationship between each precondition entity and each usage and dosage entity in the linear entity relationship, the precondition merging result and the usage and dosage merging result are combined, and the obtained root node set is:{[PP1] [MM1 MM2] [PP2] [MM3 MM4]; [PP1] [MM1 MM2] [PP2] [MM3 MM4]; [PP1] [MM1] [PP2] [MM2 MM3] [MM4]; [PP1] [MM1] [PP2] [MM2 MM3] [MM4]; [PP1] [MM1 MM2] [PP2] [MM3 MM4]; [PP1] [MM1 MM2] [PP2] [MM3 MM4]}, where [PP1] [MM1 MM2] [PP2] [MM3 MM4] is a set element.

Step 404: Merge all different set elements in the root node set.

In this alternative implementation, different set elements in the root node set are merged (for example, two by two, one by three, etc.) to obtain merging results. It should be noted that merging all different set elements in the root node set refers to merging all mergeable different set elements in the root node set, for example, different set elements that do not meet the preset rule are not merged.

Step 405: Take the merging result with the highest merging probability among merging results of the root node set as the parsing result, and add the parsing result to the knowledge graph.

In this optional implementation, N merging results are obtained by merging different set elements in the root node set. The N merging results are classified, a frequency of occurrence of each type is calculated, and the frequency is normalized to obtain a corresponding proportion of each type of merging result. For all the proportions of multiple types of merging results of a certain root node set, a probability of each type of merging result is calculated, and the merging result with the highest probability is the final parsing result.

Specifically, in this alternative implementation, the identified different precondition entities are first merged to obtain a precondition merging result, where $M_{PP}$ ($M_{PP}>1$ or $M_{PP}$=1) types of merging results may appear in this process. Second, the identified different usage and dosage entities are merged to obtain a usage and dosage merging result, where $N_{MM}$ ($N_{MM}$>1) types of merging results may appear in this process. After the two steps, only two types of elements in the precondition merging result and the usage and dosage merging result appear in the original linear entity relationship. The two types of elements are combined into set elements of the root node set, where $P_S$ ($P_S$>1) types of set elements may appear in this process. Finally, all mergeable set elements are merged, a total of $M_{PP} \times N_{MM} \times P_S$ merging results may appear, and a merging result with the highest probability among the merging results is selected as the parsing result.

According to the method for generating a drug knowledge graph provided by this alternative implementation, when the entities includes precondition entities and usage and dosage entities, the precondition entities in the linear entity relationship are identified, and the precondition entities are merged to obtain a precondition merging result; the usage and dosage entities in the linear entity relationship are identified, and the usage and dosage entities are merged to obtain a usage and dosage merging result; based on the positional relationship between each precondition entity and each usage and dosage entity in the linear entity relationship, the precondition merging result and the usage and dosage merging result are combined to obtain a root node set, all different set elements in the root node set are merged, a merging result with the highest merging probability among the merging results of the root node set is taken as a parsing result, and the parsing result is added to the knowledge graph. Therefore, the comprehensiveness of entities in the drug text is ensured by synthesizing the precondition merging result and the usage and dosage merging result; and a merging result with the highest merging probability among the merging results of the root node set is taken as the parsing result, which ensures the accuracy of generation of the drug knowledge graph. With the method, the knowledge graph in the medical field can be improved and knowledge mining can be achieved.

Figure 5:
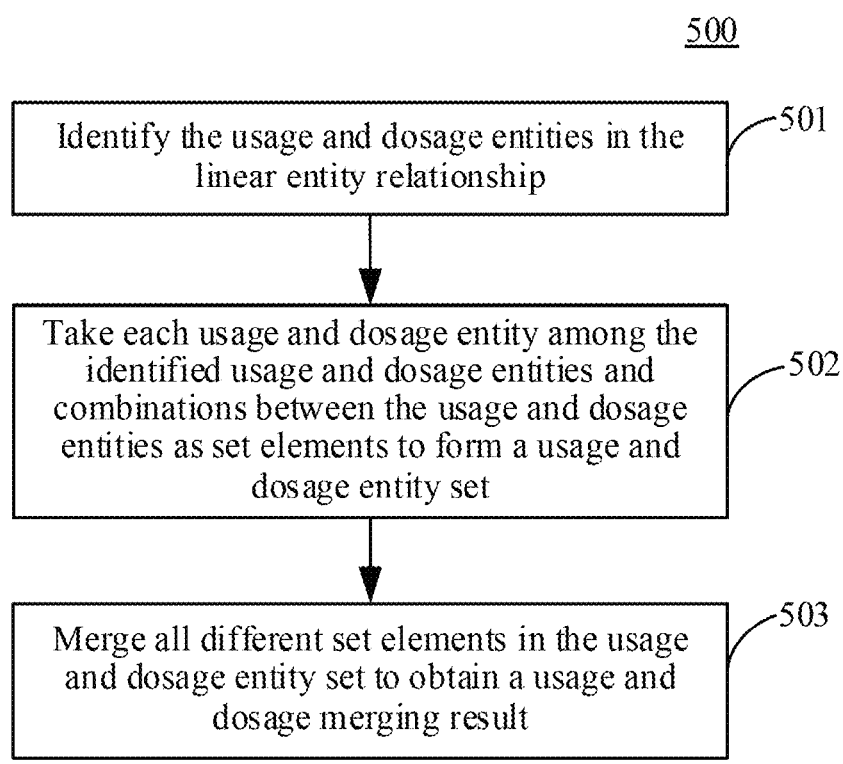
FIG. 5 is a flowchart of an embodiment of a method for obtaining a usage and dosage merging result according to the present disclosure.

In some alternative implementations of this embodiment, further reference is made to FIG. 5, which shows a flow 500 of an embodiment of a method for obtaining a usage and dosage merging result. The method for generating the drug knowledge graph includes the following steps.

Step 501: Identify the usage and dosage entities in the linear entity relationship.

In this embodiment, the usage and dosage entities are entities related to drug usage, such as dosage, frequency, treatment course, administration route, administration time, and conjunctions between the aforementioned five. The usage and dosage sub-phrase may include one or more usage and dosage entities, for example, the usage and dosage entities in the linear entity relationship include: "1 time 1 day", "1 tablet 1 time", and "1 time 1 day or 2 tablets 1 time".

Step 502: Take each usage and dosage entity among the identified usage and dosage entities and combinations between the usage and dosage entities as set elements to form a usage and dosage entity set.

In this alternative implementation, the set elements in the usage and dosage entity set include: usage and dosage entities or combinations between the usage and dosage entities.

For example, the usage and dosage entities in the linear entity relationship include: "1 time 1 day", "1 tablet 1 time", "1 time 1 day", "2 tablets 1 time".

The combinations between the usage and dosage entities may include: <1 time 1 day> or <1 tablet 1 day, 1 tablet 1 time> or <1 time 1 day, 2 tablets 1 time>.

Step 503: Merge all different set elements in the usage and dosage entity set to obtain a usage and dosage merging result.

In this alternative implementation, merging all different set elements in the usage and dosage entity set may be implemented by combining a rule analysis method and a statistical analysis method. The rule analysis method is to comply with preset rules, for example, one of the preset rules for merging the usage and dosage entity set is: the usage and dosage entity set can only include dosage set elements, frequency set elements, treatment course set elements, administration route set elements, and administration time set elements. The dosage set elements include: a single dosage or multiple dosages connected by conjunctions. The frequency set elements include: a single frequency or multiple frequencies connected by conjunctions. The treatment course set elements include: a single treatment course or multiple treatment courses connected by conjunctions. The administration route set elements include: a single administration route or multiple administration routes connected by conjunctions. The administration time set elements include: a single administration time or multiple administration times connected by conjunctions.

Alternatively, another preset rule for merging the usage and dosage entity set is: the same type of set elements cannot be merged.

For example: a usage and dosage entity set MM includes: "once a day (MM1), two tablets at a time (MM2); once a day (MM3), one tablet at a time (MM4)", where MM1 to MM4 are set elements of the usage and dosage entity set MM, MM1 and MM3 are frequency set elements and cannot be merged, and MM2 and MM4 are dosage set elements and cannot be merged.

The statistical analysis method may be an exhaustive method. The exhaustive method is to try all the possibilities. In the software, the outer loop is used to wrap the inner loop. When a certain jumping condition is satisfied, the inner loop and the outer loop are ended.

A specific example of the statistical analysis method is as follows: for all mergeable set elements in the usage and dosage entity set MM, taking each set element as a starting item, the following merging operation is performed: merging all set elements that can be adjacent to the starting item, then continuing to merge the set elements that have not been merged until all mergeable set elements in the usage and dosage entity set MM are merged, and returning to re-determine the starting item.

The usage and dosage merging result of the above usage and dosage entity set MM is: {[MM1 MM2] [MM3 MM4]; [MM1, MM2] [MM3 MM4]; [MM1][MM2 MM3][MM4]; [MM1][MM2 MM3] [MM4]; [MM1 MM2] [MM3 MM4]; [MM1 MM2] [MM3 MM4]}.

According to the method for obtaining a usage and dosage merging result provided by this alternative implementation, after usage and dosage entities are identified, each usage and dosage entity among the identified usage and dosage entities and combinations between the usage and dosage entities are taken as set elements to form a usage and dosage entity set, and all different set elements in the usage and dosage entity set are merged to obtain a usage and dosage merging result, thereby providing a reliable sentence parsing mode for forming a tree-like entity relationship from the usage and dosage entities and ensuring the reliability of a drug graph generated.

Figure 6:
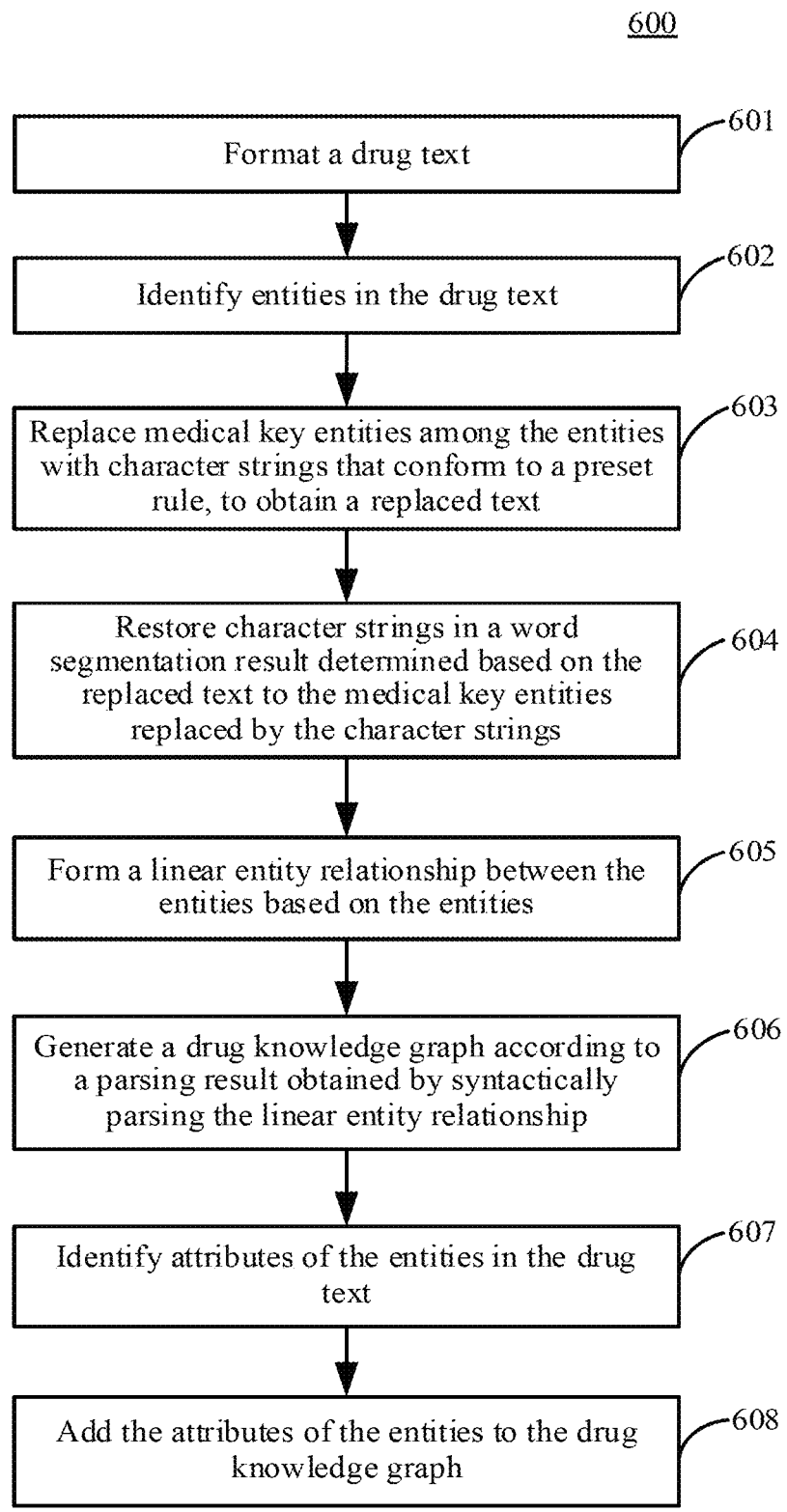
FIG. 6 is a flowchart of a third embodiment of a method for constructing a drug knowledge graph according to the present disclosure.

With further reference to FIG. 6, a flow 600 of another embodiment of a method for constructing a drug knowledge graph according to the present disclosure is shown. The method for constructing a drug knowledge graph includes the following steps.

Step 601: Format a drug text.

The formatting process may include at least one item of: 1) normalizing different punctuation marks representing the same meaning in the drug text; or 2) converting Chinese numbers in the drug text into Arabic numbers.

In this embodiment, the normalizing process is used to unify the punctuation marks representing the same meaning. When the source of the drug text is complex, the punctuation marks representing the same meaning may not be expressed uniformly in the drug text. The normalizing process ensures the unity of different punctuation marks with the same meaning. For example, "~", "-", and "—" are normalized into "-".

In this embodiment, the punctuation marks include but are not limited to: full stops, commas, slight-pause marks, quotation marks, brackets, etc. The punctuation marks of various expression ranges all fall within the protection scope of the present disclosure.

In the present embodiment, the punctuation marks include but not limited to: full stop, comma, stop, quotation marks, brackets, and the like. Punctuation marks of various expression ranges are within the protection scope of the present disclosure.

In this embodiment, some habitual expressions in Chinese may increase the difficulty in generating a knowledge graph subsequently. Therefore, all Chinese numbers need to be converted into Arabic numbers. For example, a drug text is: "once every two days, four-fifths tablet or one and a half tablets at a time". The text after Chinese numbers are converted into Arabic numbers is: "1 time 2 days, 4/5 tablet or 1.5 tablets 1 time".

Step 602: Identify entities in the drug text.

Step 603: Replace medical key entities among the entities with character strings that conform to a preset rule, to obtain a replaced text.

Step 604: Restore character strings in a word segmentation result determined based on the replaced text to the medical key entities replaced by the character strings.

In some alternative implementations of this embodiment, after the replaced text is obtained, a mapping relationship table between the character strings and the medical key entities replaced by the character strings may be established. When the medical key entities are restored, the medical key entities replaced by the character strings are restored based on the mapping relationship table.

Step 605: Based on the entities, form a linear entity relationship between the entities.

In some alternative implementations of this embodiment, the method may further include: identifying medical non-key entities in the word segmentation result. Based on the entities, forming a linear entity relationship between the entities includes: sorting the medical key entities and the medical non-key entities according to the order of the entities in the drug text, to obtain the linear entity relationship corresponding to the drug text.

Further, in some alternative implementations of this embodiment, the medical key entities include: disease name and drug name; and the medical non-key entities include: crowd, dosage, frequency, treatment course, administration route, and administration time.

Step 606: Generate a drug knowledge graph according to a parsing result obtained by syntactically parsing the linear entity relationship.

In some alternative implementations of this embodiment, the entities include precondition entities and usage and dosage entities, and the precondition entities include medical key entities. The Step 606 includes: obtaining a precondition merging result based on the precondition entities obtained by identifying the linear entity relationship; obtaining a usage and dosage merging result based on the usage and dosage entities obtained by identifying the linear entity relationship; based on the positional relationship between each precondition entity and each usage and dosage entity in the linear entity relationship, combining the precondition merging result and the usage and dosage merging result to obtain a root node set in which at least one element in the precondition merging result and at least one element in the usage and dosage merging result are used as set elements; merging all different set elements in the root node set; and taking a merging result with the highest merging probability among merging results of the root node set as the parsing result, and adding the parsing result to the knowledge graph.

It should be understood that the operations and features in steps 602-604 correspond to those in steps 201-205 above respectively. Therefore, the descriptions of the operations and features in steps 201-205 are also applicable to steps 602-604, and details are not repeated here.

Step 607: Identify attributes of the entities in the drug text.

In this embodiment, each entity in the drug text has its corresponding attribute. For example, the original text of the drug text is: "children aged 2-5", and the identified attribute result is: {"crowdType": "child", "crowdAgeFrom": 2, "crowdAgeTo": 5. "crowdAgeUnit": "Age"}.

Step 608: Add the attributes of the entities to the drug knowledge graph.

Specifically, see Table 1, which shows entities, descriptions of the entities, and attributes of the entities in a drug knowledge graph.

TABLE 1

| Entity | Description | Attribute |
|---|---|---|
| Crowd | Object of drug treatment | Age, weight, whether renal insufficiency, whether hepatic insufficiency, whether special crowds |
| Disease name | Disease name, usually indication | None |
| Drug name | Drug name | None |
| Dosage | Number of drugs used | Minimum dosage, maximum dosage, dosage unit, dosage time attribute (daily dosage/single dosage), dosage state attribute (first dosage/maintained dosage) |
| Frequency | Frequency of drug use | Time start value, time end value, time unit, minimum number of times, maximum number of times |
| Course of treatment | Duration of drug use | Time start value, time end value, time unit |
| Administration route | How to use the drug | Enumerated values: oral, eyes drop, nasal drip, . . . |
| Administration time | Time of drug use | Enumerated values: morning, noon, before dinner, . . . |
| Conjunction | Words expressing context | Negative: can't, shouldn't, . . . Transition: but, however, . . . Juxtaposition: and, or, . . . Time relationship: day 1, day 2, . . . |

In this embodiment, adding the attribute of each entity to the drug knowledge graph can ensure the comprehensiveness of entity information in the drug knowledge graph.

According to the method for constructing a drug knowledge graph provided by this embodiment, before all entities in the drug text are identified, the drug text is formatted to ensure the efficiency of entity identification. The attributes of the entities in the drug text are identified, and the identified attributes of the entities are added to the drug knowledge graph, thereby enriching the content of the drug knowledge graph and ensuring the comprehensiveness of information of the drug knowledge graph.

Figure 7:
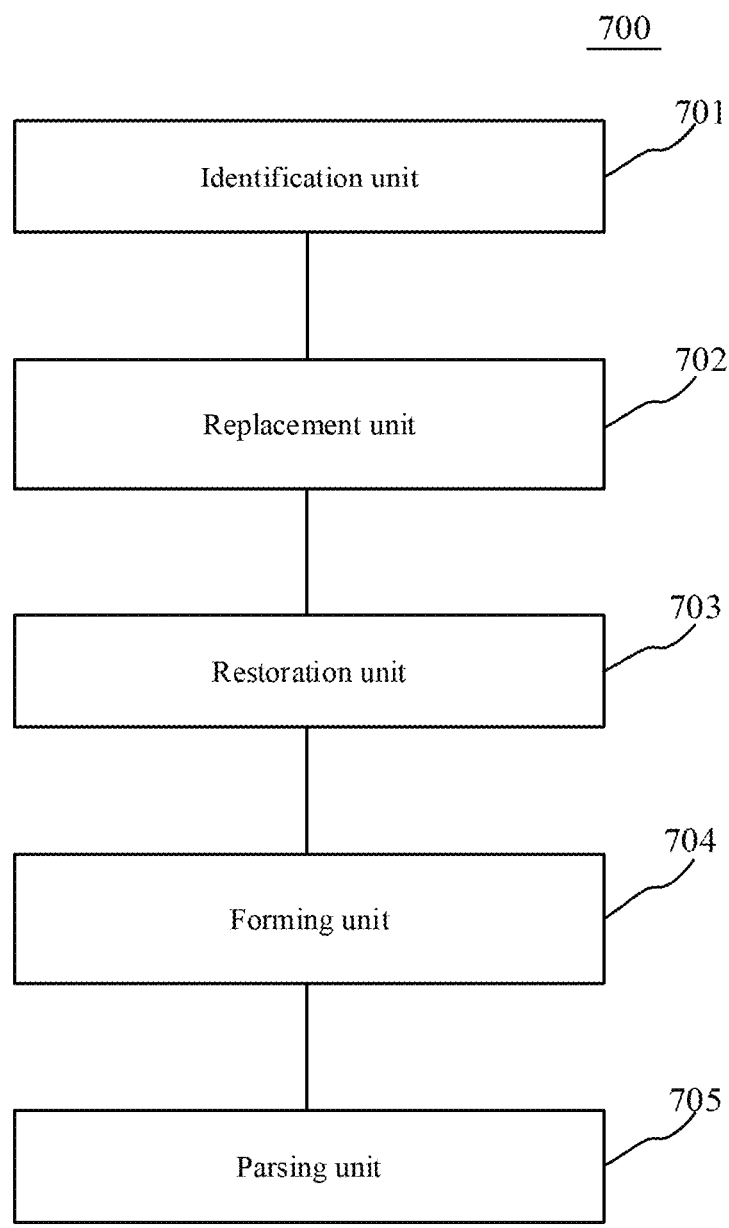
FIG. 7 is a schematic structural diagram of an embodiment of an apparatus for constructing a drug knowledge graph according to the present disclosure.

With further reference to FIG. 7, as an implementation of the methods shown in the above figures, the present disclosure provides an embodiment of an apparatus for constructing a drug knowledge graph. The embodiment of the apparatus corresponds to the embodiment of the method shown in FIG. 2, and the apparatus may be applied to various electronic devices.

As shown in FIG. 7, an embodiment of the present disclosure provides an apparatus 700 for constructing a drug knowledge graph. The apparatus 700 includes an identification unit 701, a replacement unit 702, a restoration unit 703, a forming unit 704 and a parsing unit 705. The identification unit 701 may be configured to identify entities in a drug text. The replacement unit 702 may be configured to replace medical key entities among the entities with character strings that conform to a preset rule, to obtain a replaced text. The restoration unit 703 may be configured to restore character strings in a word segmentation result determined based on the replaced text to the medical key entities replaced by the character strings. The forming unit 704 may be configured to, based on the entities, form a linear entity relationship between the entities. The parsing unit 705 may be configured to generate a drug knowledge graph according to a parsing result obtained by syntactically parsing the linear entity relationship.

In this embodiment, in the apparatus 700 for constructing a drug knowledge graph, the specific processing of the identification unit 701, the replacement unit 702, the restoration unit 703, the forming unit 704 and the parsing unit 705 and the technical effects brought thereby may be referred to steps 201, 202, 203, 204 and 205 in the embodiment corresponding to FIG. 2.

In some embodiments, the apparatus 700 further includes: a mapping unit (not shown in the figure). The mapping unit may be configured to establish a mapping relationship table between the character strings and the medical key entities replaced by the character strings.

In some embodiments, the apparatus 700 further includes: a distinguishing unit (not shown in the figure). The distinguishing unit may be configured to identify medical non-key entities in the word segmentation results; and the forming unit 704 is further configured to sort the medical key entities and the medical non-key entities according to the order of the entities in the drug text, to obtain the linear entity relationship corresponding to the drug text.

In some embodiments, the medical key entities include: disease name and drug name; and the medical non-key entities include: crowd, dosage, frequency, treatment course, administration route, and administration time.

In some embodiments, the entities include precondition entities and usage and dosage entities; the precondition entities include the medical key entities; and the parsing unit 703 includes: a precondition extraction module (not shown in the figure), a usage and dosage obtaining module (not shown in the figure), a combination module (not shown in the figure), a merging module (not shown in the figure), a parsing module (not shown in the figure), and an adding module (not shown in the figure). The precondition extraction module may be configured to obtain a precondition merging result based on the precondition entities obtained by identifying the linear entity relationship. The usage and dosage obtaining module may be configured to obtain a usage and dosage merging result based on the usage and dosage entities obtained by identifying the linear entity relationship. The combination module may be configured to, based on the positional relationship between each precondition entity and each usage and dosage entity in the linear entity relationship, combine the precondition merging result and the usage and dosage merging result to obtain a root node set in which at least one element in the precondition merging result and at least one element in the usage and dosage merging result are used as set elements. The merging module may be configured to merge all different set elements in the root node set. The parsing module may be configured to take a merging result with the highest merging probability among merging results of the root node set as the parsing result. The adding module may be configured to add the parsing result to the knowledge graph.

In some embodiments, the precondition extraction module includes: a pre-identification submodule (not shown in the figure), a pre-combination submodule (not shown in the figure), and a pre-merging submodule (not shown in the figure). The pre-identification submodule may be configured to identify the precondition entities in the linear entity relationship. The pre-combination submodule may be configured to take each precondition entity among the identified precondition entities and combinations between the precondition entities as set elements to form a precondition entity set. The pre-merging submodule may be configured to merge all different set elements in the precondition entity set to obtain the precondition merging result.

In some embodiments, the usage and dosage obtaining module includes: a usage and dosage identification submodule (not shown in the figure), a usage and dosage combination submodule (not shown in the figure), and a usage and dosage merging submodule (not shown in the figure). The usage and dosage identification submodule may be configured to identify the usage and dosage entities in the linear entity relationship. The usage and dosage combination submodule may be configured to take each usage and dosage entity among the identified usage and dosage entities and combinations between the usage and dosage entities as set elements to form a usage and dosage entity set. The usage and dosage merging submodule may be configured to merge all different set elements in the usage and dosage entity set to obtain the usage and dosage merging result.

In some embodiments, the above apparatus further includes: a distinguishing unit (not shown in the figure) and an adding unit (not shown in the figure). The distinguishing unit may be configured to identify attributes of the entities in the drug text. The adding unit may be configured to add the attributes of the entities to the drug knowledge graph.

In some embodiments, the above apparatus further includes: a formatting unit (not shown in the figure) and/or a conversion unit (not shown in the figure). The formatting unit may be configured to normalize different punctuation marks representing the same meaning in the drug text. The conversion unit may be configured to convert Chinese numbers in the drug text into Arabic numbers.

Figure 8:
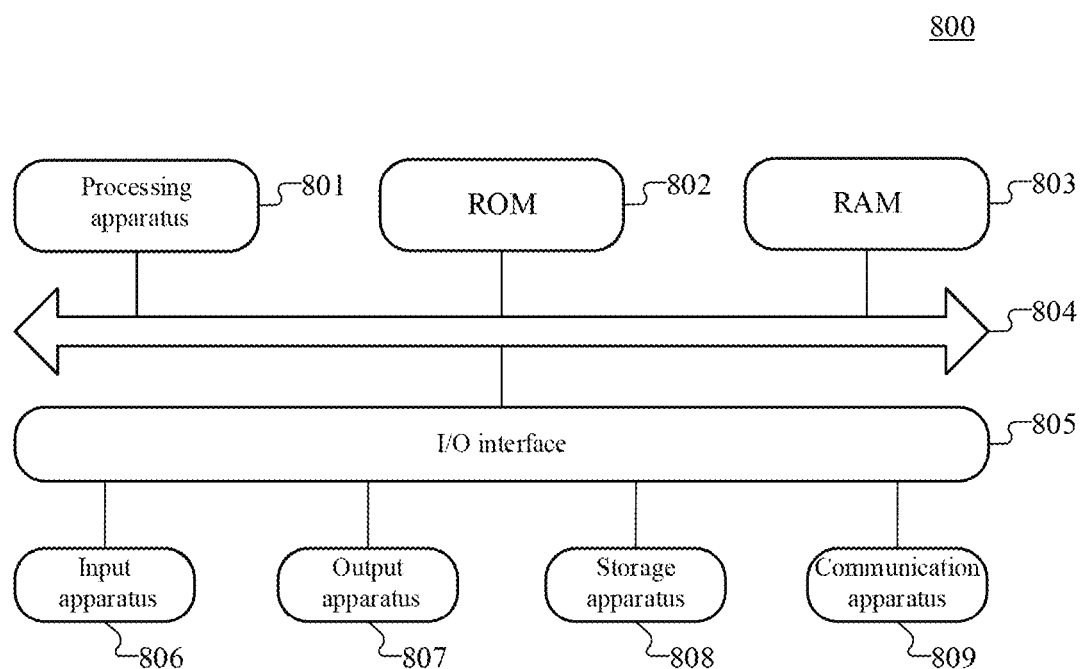
FIG. 8 is a schematic structural diagram of an electronic device adapted to implement embodiments of the present disclosure.

With reference to FIG. 8 below, a schematic structural diagram of an electronic device 800 adapted to implement the embodiments of the present disclosure is shown.

As shown in FIG. 8, the electronic device 800 may include a processing apparatus (such as CPU, and GPU) 801, which may execute various appropriate actions and processes in accordance with a program stored in a read-only memory (ROM) 802 or a program loaded into a random access memory (RAM) 803 from a storage apparatus 808. The RAM 603 also stores various programs and data required by operations of the electronic device 800. The processing apparatus 801, the ROM 802 and the RAM 803 are connected to each other through a bus 804. An input/output (I/O) interface 805 is also connected to the bus 804.

Generally, the following devices may be connected to the I/O interface 805: An input apparatus 806 including, for example, a touch screen, a touch pad, a keyboard, a mouse, or the like; an output apparatus 807 including, for example, a liquid crystal display (LCD, Liquid Crystal Display), a speaker, a vibrator, or the like; a storage apparatus 808 including, for example, a magnetic tape, a hard disk, and the like; and a communication apparatus 809. Communication apparatus 809 may allow electronic apparatus 800 to wirelessly or wirelessly communicate with other devices to exchange data. Although FIG. 8 illustrates an electronic device 800 having various devices, it should be understood that no implementation or all of the devices shown are required. More or fewer devices may alternatively be implemented or provided. Each block shown in FIG. 8 may represent one device or multiple devices as desired.

In particular, in accordance with embodiments of the present disclosure, the process described above with reference to the flowchart may be implemented as a computer software program. For example, embodiments of the present disclosure include a computer program product including a computer program embodied on a computer readable medium, the computer program comprising program code for performing the method shown in the flowchart. In such an embodiment, the computer program may be downloaded and installed from the network through the communication apparatus 809, or installed from the storage apparatus 808, or installed from the ROM 802. When the computer program is executed by the processing apparatus 801, the above functions defined in the method of the embodiment of the present disclosure are performed.

It should be noted that the computer-readable medium of the embodiments of the present disclosure may be a computer-readable signal medium or a computer-readable storage medium or any combination of the two. An example of the computer readable storage medium may include, but not limited to: electric, magnetic, optical, electromagnetic, infrared, or semiconductor systems, apparatus, elements, or a combination of any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fiber, a portable compact disk read only memory (CD-ROM), an optical memory, a magnet memory or any suitable combination of the above. In the present disclosure, the computer readable storage medium may be any physical medium containing or storing programs which may be used by a command execution system, apparatus or element or incorporated thereto. In the present disclosure, the computer readable signal medium may include data signal in the base band or propagating as parts of a carrier, in which computer readable program codes are carried. The propagating data signal may take various forms, including but not limited to: an electromagnetic signal, an optical signal or any suitable combination of the above. The signal medium that can be read by computer may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wired, optical cable, RF (Radio Frequency) etc., or any suitable combination of the above.

The computer readable medium may be included in the server; It may also be present alone and not assembled into the server. The computer-readable medium carries one or more programs that, when executed by the server, cause the server to: identifying entities in a drug text; replacing medical key entities among the entities with character strings that conform to a preset rule, to obtain a replaced text; restoring the character strings in a word segmentation result, determined based on the replaced text, to the medical key entities replaced by the character strings; forming a linear entity relationship between the entities based on the entities; and generating a drug knowledge graph according to a parsing result obtained by syntactically parsing the linear entity relationship.

A computer program code for performing operations in the present disclosure may be compiled using one or more programming languages or combinations thereof. The programming languages include population-oriented programming languages, such as Java, Smalltalk or C++, and also include conventional procedural programming languages, such as "C" language or similar programming languages. The program code may be completely executed on a user's computer, partially executed on a user's computer, executed as a separate software package, partially executed on a user's computer and partially executed on a remote computer, or completely executed on a remote computer or server. In the circumstance involving a remote computer, the remote computer may be connected to a user's computer through any network, including local area network (LAN) or wide area network (WAN), or may be connected to an external computer (for example, connected through Internet using an Internet service provider).

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion including one or more executable instructions for implementing specified logic functions. It should also be noted that, in some alternative implementations, the functions denoted by the blocks may occur in a sequence different from the sequences shown in the accompanying drawings. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system performing specified functions or operations, or by a combination of a dedicated hardware and computer instructions.

The units described in the embodiments of the present disclosure may be implemented by software or hardware. The units described may also be provided in a processor, for example, described as: a processor including an identification unit, a replacement unit, a restoration unit, a forming unit and a parsing unit. The names of these units do not constitute limitations to units themselves in some cases, for example, the identification unit may also be described as a unit "configured to identify entities in a drug text".

The above description only provides an explanation of the preferred embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the present disclosure. Technical schemes formed by the above-described features being interchanged with, but not limited to, technical features with similar functions disclosed in the present disclosure are examples.

What is claimed is:

1. A method for constructing a drug knowledge graph, the method comprising:
   identifying entities in a drug text;
   replacing medical key entities among the entities with character strings that conform to a preset rule, to obtain a replaced text;
   restoring the character strings in a word segmentation result, determined based on the replaced text, to the medical key entities replaced by the character strings;
   forming a linear entity relationship between the entities based on the entities; and
   generating a drug knowledge graph according to a parsing result obtained by syntactically parsing the linear entity relationship.

2. The method according to claim 1, further comprising:
   establishing a mapping relationship table between the character strings and the medical key entities replaced by the character strings.

3. The method according to claim 2, wherein the method further comprises: identifying medical non-key entities in the word segmentation result; and
   the forming a linear entity relationship between the entities based on the entities comprises:
   sorting the medical key entities and the medical non-key entities according to orders of the entities in the drug text, to obtain the linear entity relationship corresponding to the drug text.

4. The method according to claim 3, wherein the medical key entities comprise: disease name and drug name; and the medical non-key entities comprise: crowd, dosage, frequency, treatment course, administration route, and administration time.

5. The method according to claim 1, wherein the entities comprise precondition entities, and usage and dosage entities, and the precondition entities comprise the medical key entities;
   the generating a drug knowledge graph according to a parsing result obtained by syntactically parsing the linear entity relationship comprises:
   obtaining a precondition merging result based on the precondition entities obtained by identifying the linear entity relationship;
   obtaining a usage and dosage merging result based on the usage and dosage entities obtained by identifying the linear entity relationship;
   based on positional relationship between each precondition entity and each usage and dosage entity in the linear entity relationship, combining the precondition merging result and the usage and dosage merging result to obtain a root node set in which at least one element in the precondition merging result and at least one element in the usage and dosage merging result are used as set elements;
   merging all different set elements in the root node set; and
   taking a merging result with a highest merging probability among merging results of the root node set as the parsing result, and adding the parsing result to the drug knowledge graph.

6. The method according to claim 5, wherein the obtaining a precondition merging result based on the precondition entities obtained by identifying the linear entity relationship comprises:
   identifying the precondition entities in the linear entity relationship, and taking each precondition entity among the identified precondition entities and combinations between the precondition entities as set elements to form a precondition entity set; and
   merging all different set elements in the precondition entity set to obtain the precondition merging result.

7. The method according to claim 5, wherein the obtaining a usage and dosage merging result based on the usage and dosage entities obtained by identifying the linear entity relationship comprises:
   identifying the usage and dosage entities in the linear entity relationship, and taking each usage and dosage entity among the identified usage and dosage entities and combinations between the usage and dosage entities as set elements to form a usage and dosage entity set; and
   merging all different set elements in the usage and dosage entity set to obtain the usage and dosage merging result.

8. The method according to claim 1, further comprising:
   identifying attributes of the entities in the drug text; and
   adding the attributes of the entities to the drug knowledge graph.

9. The method according to claim 1, further comprising:
   performing at least one of following formatting processes on the drug text:
   normalizing different punctuation marks representing a same meaning in the drug text; or
   converting Chinese numbers in the drug text into Arabic numbers.

10. An apparatus for constructing a drug knowledge graph, the apparatus comprising:
    one or more processors; and
    a storage apparatus on which one or more programs are stored,
    wherein the one or more programs, when executed by the one or more processors, cause the one or more processors to perform operations, the operations comprising:
    identifying entities in a drug text;
    replacing medical key entities among the entities with character strings that conform to a preset rule, to obtain a replaced text;
    restoring the character strings in a word segmentation result, determined based on the replaced text, to the medical key entities replaced by the character strings;
    forming, based on the entities, a linear entity relationship between the entities; and
    generating a drug knowledge graph according to a parsing result obtained by syntactically parsing the linear entity relationship.

11. A non-transitory computer-readable medium storing a computer program, wherein the program, when executed by one or more processors, causes the one or more processors to perform operations, the operations comprising:

identifying entities in a drug text;

replacing medical key entities among the entities with character strings that conform to a preset rule, to obtain a replaced text;

restoring the character strings in a word segmentation result, determined based on the replaced text, to the medical key entities replaced by the character strings;

forming, based on the entities, a linear entity relationship between the entities; and generating a drug knowledge graph according to a parsing result obtained by syntactically parsing the linear entity relationship.

12. The apparatus according to claim 10, wherein the operations further comprises:

establishing a mapping relationship table between the character strings and the medical key entities replaced by the character strings.

13. The apparatus according to claim 12, wherein the operations further comprises: identifying medical non-key entities in the word segmentation result; and the forming a linear entity relationship between the entities based on the entities comprises:

sorting the medical key entities and the medical non-key entities according to orders of the entities in the drug text, to obtain the linear entity relationship corresponding to the drug text.

14. The apparatus according to claim 13, wherein the medical key entities comprise: disease name and drug name; and the medical non-key entities comprise: crowd, dosage, frequency, treatment course, administration route, and administration time.

15. The apparatus according to claim 10, wherein the entities comprise precondition entities, and usage and dosage entities, and the precondition entities comprise the medical key entities;

the generating a drug knowledge graph according to a parsing result obtained by syntactically parsing the linear entity relationship comprises:

obtaining a precondition merging result based on the precondition entities obtained by identifying the linear entity relationship;

obtaining a usage and dosage merging result based on the usage and dosage entities obtained by identifying the linear entity relationship;

based on positional relationship between each precondition entity and each usage and dosage entity in the linear entity relationship, combining the precondition merging result and the usage and dosage merging result to obtain a root node set in which at least one element in the precondition merging result and at least one element in the usage and dosage merging result are used as set elements;

merging all different set elements in the root node set; and taking a merging result with a highest merging probability among merging results of the root node set as the parsing result, and adding the parsing result to the drug knowledge graph.

16. The apparatus according to claim 15, wherein the obtaining a precondition merging result based on the precondition entities obtained by identifying the linear entity relationship comprises:

identifying the precondition entities in the linear entity relationship, and taking each precondition entity among the identified precondition entities and combinations between the precondition entities as set elements to form a precondition entity set; and merging all different set elements in the precondition entity set to obtain the precondition merging result.

17. The apparatus according to claim 15, wherein the obtaining a usage and dosage merging result based on the usage and dosage entities obtained by identifying the linear entity relationship comprises:

identifying the usage and dosage entities in the linear entity relationship, and taking each usage and dosage entity among the identified usage and dosage entities and combinations between the usage and dosage entities as set elements to form a usage and dosage entity set; and merging all different set elements in the usage and dosage entity set to obtain the usage and dosage merging result.

18. The apparatus according to claim 10, wherein the operations further comprises:

identifying attributes of the entities in the drug text; and adding the attributes of the entities to the drug knowledge graph.

19. The apparatus according to claim 10, wherein the operations further comprises:

performing at least one of following formatting processes on the drug text:

normalizing different punctuation marks representing a same meaning in the drug text; or converting Chinese numbers in the drug text into Arabic numbers.

* * * * *